United States Patent [19]

Batteux et al.

[11] Patent Number: 4,853,012
[45] Date of Patent: Aug. 1, 1989

[54] PROCESS AND DEVICE FOR DEACIDIFICATION OF A GAS CONTAINING $H_2S$ AND/OR $CO_2$ AND MERCAPTANS

[75] Inventors: Jacques Batteux; Ahmad Sharonizadeh, both of Morlaas, France

[73] Assignee: Societe Nationale ELF Aquitaine, Courbevoie, France

[21] Appl. No.: 171,003

[22] PCT Filed: Jun. 26, 1987

[86] PCT No.: PCT/FR87/00248

§ 371 Date: Feb. 25, 1988

§ 102(e) Date: Feb. 25, 1988

[87] PCT Pub. No.: WO88/00085

PCT Pub. Date: Jan. 14, 1988

[30] Foreign Application Priority Data

Jun. 30, 1986 [FR] France .................................. 86 09450

[51] Int. Cl.⁴ ............................................. B01D 53/14
[52] U.S. Cl. ............................................. 55/44; 55/48; 55/49; 55/51; 55/73; 55/222; 55/223; 423/229
[58] Field of Search ................... 55/42, 44, 48, 49, 51, 55/73, 89, 222, 223; 423/223, 228, 229

[56] References Cited

U.S. PATENT DOCUMENTS

| | | | |
|---|---|---|---|
| 2,518,752 | 8/1950 | Chapin | 423/229 |
| 2,524,088 | 10/1950 | Shaw | 423/243 |
| 3,563,695 | 2/1971 | Benson | 423/223 |
| 3,563,696 | 2/1971 | Benson | 423/223 |
| 3,622,267 | 11/1971 | Bartholome et al. | 423/229 |
| 3,642,430 | 2/1972 | Benson | 423/223 |
| 3,725,529 | 4/1973 | Giammarco et al. | 423/223 |
| 3,773,895 | 11/1973 | Thirkell | 423/223 |
| 3,961,015 | 6/1976 | Dailey | 423/229 |
| 4,160,810 | 7/1979 | Benson et al. | 423/223 X |
| 4,324,567 | 4/1982 | Ranke et al. | 55/73 X |
| 4,325,782 | 4/1982 | Grünewald et al. | 55/73 X |
| 4,372,925 | 2/1983 | Cornelisse | 55/73 X |
| 4,702,898 | 10/1987 | Grover | 423/228 X |

Primary Examiner—Robert Spitzer
Attorney, Agent, or Firm—Burgess, Ryan & Wayne

[57] ABSTRACT

The invention is a process for removing $H_2S$, $CO_2$ and mercaptans from a gas stream by liquid absorption using an absorbent wherein the mercaptans are absorbed at a high pressure and low temperature in a secondary absorption zone and separated from the absorbent by reduction of pressure after heating. The absorbent after reduction of pressure can be recycled to the absorpiton zone. The $H_2S$ and $CO_2$ are absorbed at a higher temperature than the mercaptans and are stripped from the absorbent in a regeneration zone after a reduction in pressure. The absorption zone requires two separate zones where the gas being treated passes from the high temeprature absorption zone to the low temperature zone where the mercaptans are removed.

17 Claims, 1 Drawing Sheet

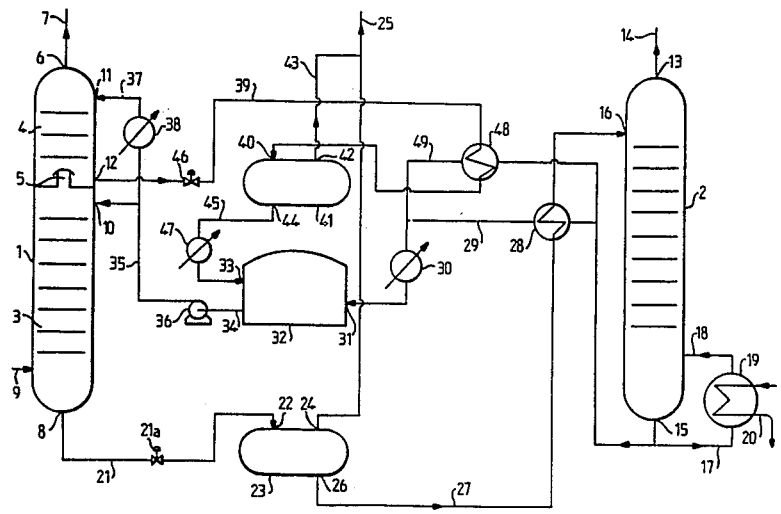

PROCESS AND DEVICE FOR DEACIDIFICATION OF A GAS CONTAINING H₂S AND/OR CO₂ AND MERCAPTANS

The invention is a process for deacidification of gas containing $H_2S$ and/or $CO_2$ and mercaptans by absorption of said compounds by means of a regeneratable absorbent solution. The invention also comprises an apparatus for carrying out the process.

BACKGROUND OF THE INVENTION

The elimination of acid compounds especially $H_2S$ and $CO_2$, contained in a gas, also called deacidification of said gas, is generally carried out by contacting the gas with an absorbent solution that retains the acid compounds by simple physical dissolution and/or by dissolution after formation of a thermally unstable salt or complex by reaction of the acid compounds with a basic compound present in the absorbent solution.

In practice, the gas to be treated, which contains the acid compounds to be removed, is brought into contact, in a zone called an absorption zone, with the absorbent solution under pressure and temperature conditions such that the absorbent solution almost entirely fixes the acid compounds, the purified gas exiting at the head of the absorption zone. The absorbent solution, charged with the acid compounds, is recovered at the bottom of the absorption zone. The charged absorbent is subjected to a regeneration treatment which separates the acid compounds from the absorbent and restores its absorbing power with respect to the acid compounds. The regeneration is carried out by introducing the charged absorbent solution from the absorption zone into the upper portion of a regeneration zone. The absorbent solution to be regenerated is maintained in this zone under temperature and pressure conditions adequate for allowing a release and/or stripping of the absorbed acid compounds. Regeneration is effected by maintaining the absorbent solution boiling under pressure in the regeneration zone. The heat needed for boiling the absorbent solution is supplied by indirect heat exchange between a portion of the solution to be regenerated, which is in the lower half of the regeneration zone, and a hot fluid at an adequate temperature, generally of saturated steam. In the course of the regeneration, the acid compounds contained in the absorbent solution to be regenerated are released and stripped by the vapors of the absorbent solution and are removed at the head of the regeneration zone. At the bottom of the regeneration zone, the regenerated absorbent solution is recovered and recycled to the absorption zone. The regenerated absorbent can be cooled by indirect heat exchange with the solution to be regenerated and recovered from the absorption zone prior to introduction into the regeneration zone.

When the gas to be deacidified contains mercaptans in addition to $H_2S$ and/or $CO_2$, the mercaptans are not substantially removed from the gas in the course of washing the gas with the absorbent solution. In fact, if the conditions are suitable for absorption of the mercaptans at the head of the absorption zone, the absorbent solution, when descending into the zone, is, on the one hand, charged with $H_2S$ and $CO_2$ by physical or chemical dissolution and on the other hand heated due to the exothermic nature of the dissolution reactions. The two phenomena cause the mercaptans that have been physically absorbed at the head of the absorption zone to be desorbed and escape for the most part into the treated gas emerging at the head of the absorption zone.

The object of the invention is to provide a process for deacidification of a gas containing $H_2S$ and/or $CO_2$ and also mercaptans by washing with a regeneratable absorbent solution which not only removes the $H_2S$ and $CO_2$ acid compounds contained in the gas but also a sufficient amount of mercaptans to provide a treated gas which can meet the specification for treated gas.

BRIEF SUMMARY OF THE INVENTION

The process according to the invention for deacidification of a gas containing $H_2S$ and/or $CO_2$ and also mercaptans comprises contacting the gas to be treated with a regeneratable absorbent liquid circulating in a countercurrent primary absorption zone, to produce a gas having a predetermined extensively reduced content of $H_2S$ and $CO_2$ and a primary stream of absorbent liquid charged with $H_2S$ and $CO_2$ and subjecting said primary stream to regeneration in a regeneration zone for releasing the absorbed acid compounds which are discharged at the head of the regeneration zone and producing at the bottom of the regeneration zone a primary regenerated absorbent liquid that is recycled to the primary absorption zone, the process being characterized by removing a fraction of the primary regenerated absorbent liquid and introducing said fraction, after having brought it to a temperature below the temperature prevailing in the primary absorption zone, into the upper portion of a countercurrent secondary absorption zone, introducing into the bottom of the secondary absorption zone, the treated gas from the primary absorption zone, collecting the purified gas at the head of the secondary absorption zone and recovering at the bottom of the secondary absorption zone, a secondary stream of absorbent liquid charged with mercaptans, subjecting said secondary stream from the secondary absorption zone to a reduction of pressure in an expansion zone so as to deabsorb the mercaptans it contains and form a secondary regenerated absorbent liquid, substantially free of mercaptans, admixing the secondary regenerated absorbent with the primary regenerated absorbent liquid and removing from the mixture, the fraction introduced into the secondary absorption zone.

The process according to the invention can be used for deacidifying all types of gases containing $H_2S$ and/or $CO_2$ and also a proportion of mercaptans that can amount up to a few percents by volume and, for example, up to 4% by volume or more, which are available under pressures going from about 10 absolute bars to about 100 absolute bars. Such a process is in particular well adapted for the treatment of different gases containing $H_2S$ and/or $CO_2$ and mercaptans in order to produce purified gases having a fixed minimal total content of sulfur.

DESCRIPTION OF THE DRAWING

The Figure is a representation of the process and apparatus utilized for carrying out the process of the invention.

DETAILED DESCRIPTION OF THE INVENTION

The absorbent liquid that can be used for carrying out the process according to the invention can be selected among the different absorbent liquids which, on the one hand, are capable of fixing $H_2S$ and $CO_2$ and then releasing said compounds under the action of heating and/or expansion and can dissolve the mercaptans and then release them under the action of an expansion optionally associated with a heating. The absorbent liquid is preferably an aqueous solution of one or more basic compounds and preferably an aqueous solution of one or more primary or secondary alkanolamines such as monoethanolamine, diethanolamine, diisopropanolamine, primary alkanolamine of the formula $HO-C_2H_4-O-C_2H_4-NH_2$ known by the name of DIGLYCOLAMINE®.

The absorbent liquid may comprise a mixture of an aqueous solution of one or more basic compounds and preferably of one or more primary or secondary alkanolamines such as mentioned above with one or more organic solvents such as sulfolane or methanol. Preferably the absorbent liquid used in the process according to the invention is an aqueous solution of one or more primary or secondary alkanolamines such as monoethanolamine, diethanolamine, diisopropanolamine or diglycolamine whose total concentration of alkanolamine is comprised between 1 N and 8 N, preferably between 3 N and 6 N.

The pressure prevailing in each one of the primary and secondary absorption zones corresponds, aside from the loss of charge, to that of the gas to be treated which is introduced in the primary absorption zone and is generally in the range of 10 bars absolute to about 100 bars absolute.

The temperature of the absorbent liquid introduced in the primary absorption zone depends on the nature of the absorbent liquid and on the dew point of the gas exiting at the head of the zone. For example, when the absorbent liquid comprises an alkanolamine aqueous solution, the temperature of the absorbent liquid introduced into the absorption zone comprises between about 10° C. and 80° C., preferably between about 20° C. and 60° C.

The supply of absorbent liquid that circulates in the primary absorption zone in countercurrent contact with the gas to be treated is related to the contents of $H_2S$ and $CO_2$ acid compounds of the gas to be treated and also to the total quantity of acid gases tolerated in the treated gas emerging at the head of the primary absorption zone. The supply of absorbent liquid introduced in the primary absorption zone is adjusted to extract substantially all the $H_2S$ and $CO_2$ acid compounds present in the gas being treated.

The pressure and temperature conditions in the regeneration zone for the primary absorbent liquid are selected to provide a regenerated absorbent liquid at the outlet of the regeneration zone be practically free of dissolved gaseous compounds. The absolute pressure at the head of the regeneration zone is generally comprised between 1 and 5 bars, most preferably between 1.3 and 2.5 bars. In the case of regeneration by re-boiling of the absorbent liquid laden with acid gas compounds, to maintain such a pressure requires a temperature at the bottom of the regeneration zone between about 100° C. and 150° C., which corresponds to a temperature at the head of the regeneration zone from about 80° C. to 125° C.

The temperature of the fraction of absorbent liquid introduced into the secondary absorption zone is equal to or sightly less than that of the absorbent liquid introduced into the primary absorption zone and such that the absorption of the mercaptans by said fraction be almost complete so that the treated gas discharged at the head of the secondary absorption zone has a total content of sulfur corresponding to the specifications required. The temperature of said fraction is preferably below 50° C. when the absorbent liquid is an aqueous solution of alkanolamine.

The amount of absorbent liquid introduced in the secondary absorption zone can vary widely and generally represents from about 20% to about 100%, preferably from about 30% to about 60%, of the supply of absorbent liquid introduced in the primary absorption zone.

In the expansion zone, the pressure on the secondary stream of absorbent liquid laden with mercaptans is reduced so that almost all the mercaptans dissolved can be released. At the bottom of the expansion zone, a regenerated secondary stream of absorbent liquid substantially free of mercaptans is produced. The regenerated secondary stream is admixed with the regenerated absorbent liquid from the regeneration zone. At the head of the expansion zone, a gas charged with mercaptans is evacuated. The secondary stream of absorbent liquid laden with mercaptan is preferably reheated prior to being introduced into the expansion zone. The reheating is preferably effected to increase the temperature of the secondary stream of absorbent liquid by about 10° to 50° C. before being introduced into the expansion zone.

Prior to introduction to the regeneration zone, the primary absorbent liquid, laden with $H_2S$ and $CO_2$ acid compounds, can be subjected to an expansion to release gases, and especially the hydrocarbons which have been physically dissolved during contact with the gas being treated. The gases released during the expansion can be used as combustible gases in heating installations or flared. The gas laden with mercaptans removed from the expansion zone that receives the secondary current of absorbent liquid can be mixed with gases released during the expansion of the primary current of absorbent liquid from the primary absorption zone.

An apparatus for carrying out the process according to the invention comprises a primary absorption column provided at the head with an outlet for the gases and at the bottom with an outlet for the liquids and equipped in its lower part, with a conduit for injection of the gas to be treated and, in its upper part, with an inlet of absorbent liquid, 2 regeneration column provided at the head with a discharge conduit for the gases and equipped at its upper part with an inlet of absorbent liquid connected to the outlet for the liquids at the bottom of the primary absorption column, at its lower part with a heating system and at the bottom with an outlet for the liquids, said outlet for the liquids being connected, via a recycling system, to the inlet of absorbent liquid of the primary absorption column, is characterized in that it also includes a secondary absorption column having at the head an outlet for the gases which extends by a conduit and at the bottom an outlet for the liquids, said secondary column being provided at its lower part with a gas inlet connected to the outlet for the gases at the head of the primary absorption column and at its upper part with an inlet of absorbent liquid fed by the recycling system, and an expansion vessel including at the top an outlet orifice for the gases connected to a discharge conduit and at the bottom an outlet orifice for the liquid connected to a drawing off conduit for transporting the liquid to the recycling system, said expansion vessel having in addition an inlet orifice for liquid connected by a conduit, provided with a pressure regulation valve to the outlet for the liquids from the secondary absorption column.

The primary absorption column and the secondary absorption column advantageously form two superposed sections of the same absorption column, the secondary absorption column constituting the upper section of said single absorption column, said sections communicating by a passage for the gases that empties into the upper section which comprises the secondary column above the outlet for the liquids situated at the bottom of said secondary column.

The system for recycling absorbent liquid preferably comprises a storage tank having one or more inlets connecting said tank to the outlet for the liquids at the bottom of the regeneration column via a conduit preferably equipped with a cooling system, to the draw off conduit associated with the expansion vessel and optionally to a conduit for feeding additional absorbent liquid and an outlet connected by a conduit to the inlet of absorbent liquid to the primary absorption column, said conduit carrying a shunt provided with a cooling system for indirect exchange of heat and connected to the inlet of absorbent liquid to the secondary absorption column, there being provided means in the conduits to the storage tank and leaving the latter for ensuring the circulation of the absorbent liquid.

The conduit that connects the outlet for the liquids of the secondary absorption column to the expansion vessel is preferably equipped with a heating system positioned either upstream or downstream of the valve for regulation of pressure mounted on said conduit. The heating system preferably comprises an indirect heat exchanger whose cold side is serially arranged on the conduit that connects the outlet for the liquids of the secondary absorption column to the expansion vessel and the hot side is serially arranged in the conduit that connects the outlet of the liquids at the bottom of the regeneration column to the storage tank forming the recycling system or on a shunt mounted on said conduit.

The connection between the outlet for the liquids at the bottom of the primary absorption column and the inlet of absorbent liquid present in the upper part of the regeneration column can be effected through an expansion vessel which includes at the top an outlet for the gases connected to a conduit for gas discharge and at the bottom an outlet for the liquids connected by a conduit to the inlet of liquid to the regeneration column, said expansion vessel having in addition an inlet for the liquids connected by a conduit to the outlet for the liquids at the bottom of the primary absorption column. In this case, the discharge conduit for gas associated with the expansion vessel is preferably connected to the discharge conduit for gas associated with the expansion vessel from the secondary absorption zone.

Each one of the absorption and regeneration columns that form part of the apparatus according to the invention can be of any type known that is usually employed for putting into contact a gas with a liquid and can consist, for example, of a column of plates or with packing.

The number of plates or the equivalent height of packing of the columns used is chosen so that in operation, each one of the columns correctly plays its part in order to obtain the desired degree of purification of the gas to be treated and the desired level of regeneration of the absorbent liquid charged with acid impurities.

The invention will be better understood by the description which follows of one embodiment illustrated by the figure of the enclosed drawing of an apparatus according to the invention which makes use of columns of plates.

Referring to the figure, the device for deacidifying a gas containing $H_2S$ and/or $CO_2$ and mercaptans includes two columns, namely, one absorption column 1 and one regeneration column 2, each one equipped with plates for gas/liquid contact. The column 1 is comprised of two superposed absorption sections, namely, one lower primary absorption section 3 and one upper secondary absorption section 4, said sections communicating by a passage 5 for the gases. One outlet 6 for the gases is provided at the top of the column 1, that is at the top of the secondary absorption section, said outlet being connected to a gas discharge conduit 7. One outlet 8 for the liquid is provided at the bottom of the column 1, that is, at the bottom of the primary absorption section. In its lower part, that is, in the lower part of the primary absorption section, the column 1 is equipped with a conduit 9 of injection of the gas to be treated. Said column 1 includes also, at the upper part of each one of the primary and secondary absorption sections, an inlet, respectively 10 and 11, for absorbent liquid while one outlet 12 for liquid is provided at the bottom of the secondary absorption section.

The regeneration column 2 is provided at the top with an outlet 13 for the gases connected to a gas discharge conduit 14 and at the bottom with an outlet 15 for the regenerated absorbent liquid. In its upper part, the regeneration column 2 is provided with an inlet 16 for absorbent liquid to be regenerated while in its lower part said column is associated by inlet and outlet pipes 17 and 18 with a re-boiler 19 heated by indirect exchange of heat by means of saturated steam flowing in a heat exchange line 20.

The outlet 8 for the liquids of the column 1 is connected by a conduit 21 provided with a pressure regulation valve 21a to the inlet 22 for the liquids of an expansion vessel 23. Said expansion vessel is provided with an outlet 24 for the gases connected to a gas discharge conduit 25 and with an outlet 26 for the liquids. The outlet 26 being connected by a conduit 27, via the cold side of an indirect heat exchanger 28, to the inlet 16 of the regeneration column 2.

The outlet 15 for the liquid of the regeneration column 2 is connected by a conduit 29, through the hot side of the heat exchanger 28 and then through a cooling system 30, to a first inlet 31 of a tank 32 for storage of absorbent liquid, said tank having a second inlet 33 and an outlet 34. Said outlet 34 is connected by a conduit 35 and a pump 36, to the inlet 10 of absorbent liquid to the primary absorption section 3 of the column 1. A conduit 37, connected to the conduit 35 downstream of the pump 36 is connected, through a cooling system 38, to the inlet 11 of absorbent liquid of the secondary absorption section 4 of the column 1. The outlet 12 for the liquid from said secondary absorption section 4 is connected to the inlet 40 for the liquid of an expansion vessel 41 by a conduit 39 equipped with a pressure regulation valve 46. The conduit 39 is serially connected to the cold side of an indirect heat exchanger 48 whose hot side is serially connected to a conduit 49 which is shunt connected to conduit 29 upstream of the cooling system 30. The expansion vessel 41 is in addition provided with outlet 42 for the gases which is connected to a conduit 43 for gas discharge connected to the conduit 25 and with an outlet 44 for the liquid connected by a conduit 45 equipped with a cooling system 47, to the second inlet 33 of the storage tank.

The operation of this device can be diagrammatically explained as follows:

The gas to be treated, such as a natural gas, which contains the acid compounds to be removed, namely, $H_2S$ and/or $CO_2$ and mercaptans is introduced under an elevated pressure, for example, in the range of from 40 to 80 absolute bars, by the conduit 9 into the primary absorption section 3 of the column 1 and is countercurrently contacted with the absorbent liquid, regeneratable by heating, which is introduced in said primary section 3 through the inlet 10 from the storage tank 32, and flows by gravity in the primary absorption section 3. In this absorption section the absorbent liquid fixes almost all the $H_2S$ and $CO_2$ acid compounds and only a small amount of the mercaptans present in the gas to be treated. Said gas, upon reaching the upper part of the primary absorption section 3, leaves through passage 5 and enters the secondary absorption section 4 where it comes into countercurrent contact with the fraction of the absorbent liquid that is conveyed by the conduit 37 through the cooling system 38 and is introduced into the secondary absorption section 4 through inlet 11. The temperature of this fraction of absorbent liquid is reduced, during its passage through the cooling system 38, to a value below the temperature of the stream of absorbent liquid entering the primary absorption section 3 and such that said cooled fraction of absorbent liquid, in the course of its descent by gravity in the secondary absorption section 4, fixes by dissolution the desired quantity of mercaptans present in the gas. At the top of the secondary absorption section 4, a purified gas that is discharged through outlet 6 and conduit 7, said gas having residual contents of $H_2S$ and $CO_2$ acid compounds and mercaptans that have been lowered to the required values.

The absorbent liquid laden with $H_2S$ and $CO_2$ acid gaseous compounds and with a small quantity of mercaptans absorbed in the primary absorption section 3 of column 1 issues from said column through the outlet 8 and reaches, by the conduit 21, the expansion vessel 23 wherein the pressure of said absorbent liquid is lowered and gaseous compounds are released from the absorbent, especially hydrocarbons and mercaptans, physically dissolved by the absorbent liquid, said gaseous compounds being discharged through the conduit 25. The current of absorbent liquid charged with $H_2S$ and $CO_2$ acid compounds whose pressure has been reduced in the expansion vessel 23 is then conveyed to the regeneration column 2, by the conduit 27 after reheating in the heat exchanger 28. In the regeneration column the absorbent liquid is kept boiling under a pressure above the atmospheric pressure and generally comprised between 1 and 5 absolute bars, so as to release the acid gaseous compounds absorbed and to strip them by the vapors of the absorbent liquid. The regenerated absorbent liquid is removed from the regeneration column 2 through outlet 15 at the bottom of the column and is recycled to the storage tank 32 through conduits 29 and 49 under the action of a pump (not shown), after having been cooled to the temperature appropriate for the primary absorption by passage through heat exchangers 28 and 48 for transferring the heat respectively to the absorbent liquid to be regenerated conveyed by the conduit 27 to the regeneration column and to the secondary stream of absorbent liquid laden with mercaptans, and then through cooling system 30. The calories needed for boiling the absorbent liquid in the regeneration column are supplied by passage of part of the regenerated liquid removed through outlet 15 into the re-boiler 19 heated by saturated steam passing into the pipe 20 and return of the hot absorbent liquid to the regeneration column by pipe 18.

The $H_2S$ and $CO_2$ gaseous compounds released in the regeneration column are stripped by the vapors of the absorbent liquid and exit at the top of said column through outlet 13 for discharge through conduit 14.

The secondary stream of absorbent liquid charged with mercaptans in the secondary absorption section 4 exits from the secondary section through outlet 12 at the bottom of the section. The absorbent liquid is then conveyed by the conduit 39 into the expansion vessel 41 after being reheated in heat exchanger 48. In vessel 41, the pressure of the liquid is sufficiently reduced so that substantially all the mercaptans dissolved in the absorbent liquid are released, said mercaptans being discharged from expansion vessel 41 through outlet 42 and conduit 43 and mixed with the discharged gases in conduit 25. The absorbent liquid substantially free of mercaptans is removed from the expansion vessel 41 through outlet 44 and returned by the conduit 45, after cooling in the cooling system 47, to the storage tank 32 wherein said absorbent liquid is mixed with the regenerated absorbent liquid from regeneration column 2.

An example of the process according to the invention, which example is not limiting, is given below.

EXAMPLE

A natural gas consisting mostly of methane and containing, by volume, 0.5% $H_2S$ and 5% $CO_2$, and 200 mg/Nm$^3$ methyl mercaptan and ethyl mercaptan by way of impurities is treated by an apparatus and process analogous to the one described with reference to the figure of the enclosed drawing.

The absorption column included a primary absorption section and a secondary absorption section respectively containing 20 and 5 plates and the regeneration column included 21 plates.

The absorbent liquid consisted of a diethanolamine aqueous solution (abbreviated DEA) containing 3 moles DEA per liter.

The natural gas to be treated entered the primary absorption section 3 through conduit 9 at a rate of 62,000 Nm$^3$/h, an absolute pressure of 75 bars and a temperature of about 35° C. The gas was countercurrently contacted with the DEA aqueous solution introduced into primary absorption section 3 through inlet 10 at a rate of 60 m$^3$/h and a temperature of about 40° C. In the primary absorption section, almost all the $H_2S$ and $CO_2$ acid compounds are absorbed in the DEA aqueous solution, the solution absorbing in this section only a very small part of the mercaptans. Having reached the upper part of the primary absorption section 3, the gas, in the course of treatment, entered the secondary absorption section 4 and was countercurrently contacted by the fraction of DEA aqueous solution introduced into the secondary absorption section through inlet 11 at a rate of 30 m$^3$/h and a temperature of about 37° C.

In this secondary absorption section, almost all the mercaptans were absorbed by the cooled DEA aqueous solution, and the residual quantities of $H_2S$ and $CO_2$ present in the gas were removed.

A deacidified natural gas containing, by volume, 2.5 ppm $H_2S$ and 100 ppm $CO_2$ and 80 mg/$Nm^3$ mercaptans was discharged through outlet 6 of column 1.

The DEA aqueous solution at the bottom of the regeneration column was raised to a temperature of about 125° C. by saturated steam under an absolute pressure of 4 bars through pipe 20 of the re-boiler 19 so as to maintain an absolute pressure of 2.2 bars at the top of the regeneration column.

Through outlet 13, at the top of the regeneration column 2, there was discharged 2,300 $Nm^3$/h of an acid gas formed by the acid gases released in the course of the regeneration of the DEA solution containing by volume 14% $H_2S$ and 85% $CO_2$, the rest consisting of water vapor.

The reduction of pressure of the DEA aqueous solution charged with $H_2S$ and $CO_2$ in the expansion vessel 23 released 50 $Nm^3$/h of a gas consisting essentially of methane, said gas being discharged through conduit 25.

Through outlet 12 of the secondary absorption section 4, 30 $m^3$/h of DEA solution charged with mercaptans were removed. The solution was at a temperature of about 37° C. and an absolute pressure of 74.5 bars. The solution was conveyed, after reheating to about 60° C., in heat exchanger 48, into the expansion vessel 41 wherein the pressure of the solution was lowered to about 2.5 bars absolute. The expansion of the solution released almost all the dissolved mercaptans which were discharged through outlet 42 of expansion vessel 41 and discharge conduit 43. The DEA aqueous solution, practically rid of the mercaptans, was drawn off through outlet 44 and conduit 45 and conveyed, at a rate of 30 $m^3$/h, to storage tank 32. The solution was at a temperature of about 40° C. at the exit of cooling system 47.

In a comparison test, the natural gas having the above mentioned composition was treated by operating under conditions similar to those defined above, but replacing the absorption column 1 having two absorption sections, primary and secondary, by an absorption column having a single absorption section including 25 plates, single injection of the solution with a delivery of 90 $m^3$/h and a temperature of about 40° C. and regeneration of the total DEA aqueous solution laden with absorbed acid compounds in the regeneration column 2 operating by re-boiling.

The treated gas at the top of the absorption column contained, by volume, 2.5 ppm $H_2S$ and 100 ppm $CO_2$ and 180 mg/$Nm^3$ mercaptans.

What is claimed is:

1. In a process for the deacidification of a gas containing $H_2S$ and/or $CO_2$ and mercaptans wherein the gas to be treated is contacted countercurrently with a regeneratable absorbent liquid in a primary absorption zone to produce a gas having a reduced content of $H_2S$ and $CO_2$ and a primary stream of absorbent liquid charged with $H_2S$ and $CO_2$, and said primary stream of absorbent liquid is subjected to regeneration in a regeneration zone to release the $H_2S$ and $CO_2$ acid compounds that have been absorbed, to produce a primary regenerated absorbent liquid that is recycled to the primary absorption zone, the improvement which comprises: separating a fraction of the recycled, primary regenerated absorbent liquid; cooling the separated fraction of recycled primary absorbent liquid to a temperature below the temperature of the primary absorption zone; introducing the cooled separated fraction into a secondary absorption zone at the upper part thereof; injecting the gas from the primary absorption zone into the lower part of the secondary absorption zone; countercurrently contacting the gas from the primary absorption zone with the separated fraction to remove mercaptans and produce a purified gas; collecting the purified gas from the secondary absorption zone; removing a secondary stream of absorbent liquid charged with mercaptans from the secondary absorption zone; reducing the pressure on the secondary absorbent liquid in an expansion zone to deabsorb the mercaptans and form a secondary regenerated absorbent liquid substantially free of mercaptans; mixing said secondary regenerated absorbent liquid with the primary regenerated absorbent liquid prior to separating the fraction of the primary regenerated absorbent liquid introduced into the secondary absorption zone.

2. A process according to claim 1, wherein the gas to be treated contains a proportion of mercaptans up to about 4% by volume.

3. A process according to claim 1, characterized in that the gas to be treated is at a pressure of from about 10 bars absolute to about 100 bars absolute.

4. A process according to claim 1, wherein the absorbent liquid comprises an aqueous solution of at least one primary or secondary alkanolamine having a total concentration of alkanolamines between about 1 N and 8 N.

5. A process according to claim 1, wherein the temperature of the separated fraction of absorbent liquid introduced into the secondary absorption zone is less than 50° C.

6. A process according to claim 1, wherein the absorbent liquid introduced into the secondary absorption zone ranges from about 20% to 100% of the amount of absorbent liquid introduced into the primary absorption zone.

7. A process according to claim 1, wherein the stream of absorbent liquid charged with mercaptans, removed from the secondary absorption zone, is heated prior to being introduced into the expansion zone.

8. A process according to claim 7, wherein the temperature of the stream of absorbent liquid charged with mercaptans is increased by about 10° C. to 50° C. prior to introducing the stream into the expansion zone.

9. An apparatus for the deacidification of a gas containing $H_2S$ and/or $CO_2$ and mercaptans by contact with a liquid absorbent which comprises: a primary absorption column (3) provided at the top (5) with an outlet for the gases and at the bottom with an outlet (8) for the liquid and equipped in its lower part with a conduit (9) for injection of the gas to be treated and at its upper part with an inlet (10) for absorbent liquid; a secondary absorption column (4) having at the top an outlet (6) for gas, said outlet in communication with a discharge conduit (7), and at the bottom an outlet (12) for liquid absorbent, the secondary column having in its lower part an inlet (5) for gas in communication with the outlet for gas at the top of the primary absorption column and in its upper part with an inlet (11) for absorbent liquid; and wherein the primary absorption column (3) and the secondary absorption column (4) form two superposed sections of a single absorption column (1), said secondary absorption column constituting the upper section of said absorption column (1), and said sections in communication by a passage (5) for the gases that enter the section (4) that comprises the secondary absorption column above the outlet (12) for the liquid; a regeneration column (2) provided at the top (13) with a conduit (14) for discharge of the gas end equipped in its upper part with an inlet (16) for absorbent liquid, which is connected to the outlet (8) for the liquids at the bottom of the primary absorption column (3), at its lower part with a heating system (19, 20) and at the bottom with an outlet (15) for the liquid; and expansion vessel (41) including at the top one orifice (42) for the gases connected to a discharge conduit (43) and at the bottom one orifice (44) for outlet of the liquid to storage tank (32), said expansion vessel having in addition one orifice (40) for entry of liquid from the secondary absorption column; and a recycling system comprised of a storage tank (32) having at least one inlet (31, 33) connecting the tank to the outlet (15) for liquid form the bottom of the regeneration column (2) through a conduit (29), and the orifice (44) for outlet of liquid at the bottom of expansion vessel (41) through drawing-off conduit (45), and an outlet (34) connected by a conduit (35) to the inlet (10) for absorbent liquid in the primary absorption column (3), the conduit (35) carrying a bypass (37) provided with a cooling system (38) connected to the inlet (11) for absorbent liquid to the secondary absorption column (4), there being provided means (36) in the conduits reaching tank (32) and departing therefrom to ensure circulation of the abosorbent liquid.

10. A device according to claim 9, wherein the conduit (39) that connects the outlet for the liquid of the secondary absorption zone (4) to the expansion vessel (41) is equipped with a heating system (48).

11. A device according to claim 10, wherein the heating system (48) comprises an indirect heat exchanger whose cold side is serially connected in the conduit (39) and the hot side is serially connected in the conduit (29) that connects the outlet (15) for the liquid at the bottom of the regeneration column (2) to the storage tank (32).

12. A device according to claim 10, wherein the heating system (48) comprises an indirect heat exchanger whose cold side is serially connected in the conduit (39) and the hot side is serially connected to a conduit (49) shunt connected to conduit (29) that connects the outlet (15) for the liquid at the bottom of the regeneration column (2) to the storage tank (32).

13. A device according to claim 9, including an expansion vessel (23) comprising at the top an outlet (24) for the gas connected to a gas discharge conduit (25) and at the bottom and outlet (26) for the liquid connected by a conduit (27) to the inlet (16) for absorbent liquid of the regeneration column, the expansion vessel (23) having in addition an inlet (22) for the liquid connected by a conduit (21) provided with a pressure regulating valve (21a) to the outlet (8) for the liquid at the bottom of the primary absorption column (3).

14. A device according to claim 13, wherein the gas discharge conduit (43) associated with the expansion vessel (41) is connected to the gas discharge conduit (25) associated with the expansion vessel (23).

15. A device according to claim 13, wherein conduit (27) is connected to the inlet (16) for absorbent liquid of the regeneration column through a cold circuit of an indirect heat exchanger (28) which hot circuit is serially connected in the conduit (29) that connects the outlet (15) for the liquid at the bottom of the regeneration column to the storage tank (32).

16. A device according to claim 9, wherein the primary absorption column (3) and the secondary absorption column (4) form two superposed sections in a single absorption column (1), said secondary absorption column constituting the upper section of said absorption column (1), said superposed sections being in communication by a passage for the gases that enter the section acting as the secondary absorption column (4) above the outlet (12) for the liquid provided in said column (4).

17. A device according to claim 9, wherein said at least one inlet (31, 33) provided in the storage tank is connected to a conduit for feeding additional absorbent liquid.

* * * * *

UNITED STATES PATENT AND TRADEMARK OFFICE
CERTIFICATE OF CORRECTION

PATENT NO. : 4,853,012
DATED : August 1, 1989
INVENTOR(S) : Jacques Batteaux, et al It is certified that error appears in the above-identified patent and that said Letters Patent is hereby corrected as shown below:

In the title page, under item [73]: the name of the Assignee should be --Societe Nationale Elf Aquitaine (Production)--.

In the Abstract, line 7: "absorpiton" should be --absorption--

Column 3, line 52: delete the word "be".

Column 4, line 46: "2" should be --a--.

Column 7, line 33: delete the word "that".

Column 10, line 68: "end" should be --and--.

Column 11, line 13: "form" should be --at--.

Signed and Sealed this

Fifth Day of February, 1991

Attest:

HARRY F. MANBECK, JR.

Attesting Officer   Commissioner of Patents and Trademarks